United States Patent [19]
Zeitlin et al.

[11] Patent Number: 5,770,764
[45] Date of Patent: Jun. 23, 1998

[54] PROCESS FOR PREPARING PURIFIED AROMATIC POLYCARBOXYLIC ACIDS

[75] Inventors: Martin A. Zeitlin, Naperville; David L. Sikkenga, Wheaton; Stephen V. Hoover, Aurora; Paul K. Behrens, Warrenville, all of Ill.

[73] Assignee: Amoco Corporation, Chicago, Ill.

[21] Appl. No.: 858,362

[22] Filed: May 19, 1997

[51] Int. Cl.⁶ ................................................. C07C 51/16
[52] U.S. Cl. ........................... 562/412; 562/414; 562/416
[58] Field of Search ..................................... 562/412, 416, 562/414

[56] References Cited

U.S. PATENT DOCUMENTS 3,870,754  3/1975  Yamashita et al. .
4,933,491  6/1990  Albertins et al. .
4,950,786  8/1990  Sanchez et al. .
5,262,560  11/1993  Behrends et al. .

*Primary Examiner*—Samuel Barts
*Attorney, Agent, or Firm*—Thomas E. Nemo; Scott P. McDonald; Wallace L. Oliver

[57] ABSTRACT

Economical processes are disclosed for preparing relatively pure polycarboxylic acid from typical crude products of liquid phase oxidation, which do not involve intermediate steps of ester formation or require any alkanol containing solvent, for purification of "crude" polycarboxylic acid containing impurities which include one or more monofunctional aromatic compounds, trifunctional aromatic compounds, and/or color causing organic compounds formed by oxidation of a corresponding substituted aromatic compound in a liquid phase, e.g. 2,6-naphthalene dicarboxylic acid by liquid phase oxidation of 2,6-dimethyl naphthalene. The invention provides integrate processes which comprise reacting crude oxidation product with a polyalkyl amine amine, e.g. trialkylamine, forming an aqueous solution of the salts thus obtained, separating deleterious compounds from the solution, and recovering the polyalkyl amine and a relatively pure polycarboxylic acid product.

20 Claims, 1 Drawing Sheet

FIG. 1

PROCESS FOR PREPARING PURIFIED AROMATIC POLYCARBOXYLIC ACIDS

FIELD OF THE INVENTION

This invention relates to integrated processes for preparing relatively pure polycarboxylic acid from typical "crude" products of liquid phase oxidation. More particularly, the invention provides economical processes which comprise reacting crude oxidation product with a polyalkyl amine component, forming an aqueous solution of the salts thus obtained, separating deleterious compounds from the solution, and recovering the polyalkyl amine and relatively pure polycarboxylic acid product. Integrated process of the invention do not involve intermediate steps of ester formation and hydrolysis, or require any alkanol containing solvent.

Crude polycarboxylic acids formed by oxidation of a corresponding substituted aromatic compound contain deleterious compounds including monofunctional impurities, color causing components, metals, and trifunctional impurities which integrated processes of the invention, advantageously, remove to provide purified products, e.g. aromatic dicarboxylic acids. Crude 2,6-naphthalene dicarboxylic acid from liquid phase oxidation contains, typically, impurities including 2-naphthoic acid, 2-methyl-6-naphthoic acid, and 6-formyl-2-naphthoic acid, and trimellitic acid. Impurities in crude terephthalic acid from liquid phase oxidation include 4-carboxybenzoic acid, benzoic acid and para-toluic acid. Integrated process of the invention are particularly suitable to purify such crude 2,6-naphthalene dicarboxylic acid and crude terephthalic acid.

BACKGROUND OF THE INVENTION

Aromatic polycarboxylic acids are highly useful organic compounds. Some are used as intermediates for the preparation of other organic compounds, and some are used as monomers for the preparation of polymeric materials. For example, terephthalic acid is used to prepare polyethylene terephthalate, a widely used polyester material and the naphthalene carboxylic adds, i.e, the naphthoic acids, are used for preparing photographic chemicals and dyestuffs. Additionally, naphthalene dicarboxylic acids can be used to prepare a variety of polyester and polyamide compositions. One such naphthalene dicarboxylic acid, 2,6-naphthalene dicarboxylic acid, is a particularly useful aromatic carboxylic acid because it can be reacted with ethylene glycol to prepare poly(ethylene-2,6-naphthalate).

Purified terephthalic acid is, for example, derived from relatively less pure, technical grade or crude terephthalic acid by purification of the latter utilizing hydrogen and a noble metal catalysts as described in U.S. Pat. No. 3,584,039 to Meyer. In the purification process, impure terephthalic acid is dissolved in water at an elevated temperature, and the resulting solution is hydrogenated, preferably in the presence of a hydrogenation catalyst, e.g., palladium on a carbon support, as described in U.S. Pat. No. 3,726,915 to Pohlmann. This hydrogenation step converts various color bodies present in the relatively impure terephthalic acid to colorless products. Another related purification-by-hydrogenation process of aromatic polycarboxylic acids produced by liquid phase catalyst oxidation of polyalkyl aromatic hydrocarbons is described in U.S. Pat. No. 4,405,809 to Stech et al. Where the desired polycarboxylic acid is less soluble in water than terephthalic acid, purification-by-hydrogenation processes are, correspondingly, less practical.

Dialkyl-2,6-naphthalene dicarboxylates and 2,6-naphthalene dicarboxylic acid are useful monomers for the preparation of high performance polymeric materials. Dimethyl-2,6-naphthalene dicarboxylate and 2,6-naphthalene dicarboxylic acid are, for example, reacted with ethylene glycol to prepare poly(ethylene-2,6-naphthalate). Fibers and films manufactured from poly(ethylene-2,6-naphthalate) have improved strength and superior thermal properties relative to other polyester materials. Films made from poly(ethylene-2,6-naphthalate) demonstrate superior resistance to gas diffusion and particularly to diffusion of carbon dioxide, oxygen and/or water vapor. Because of their exceptional properties, poly(ethylene-2,6-naphthalate) materials are, especially, suitable for applications such as food and beverage containers, particularly for tire cord, magnetic recording tape, electronic components, and so-called "hot-fill" food and beverage containers.

Although dialkyl-2,6-naphthalene dicarboxylates, more particularly purified dimethyl-2,6-naphthalene dicarboxylate, are suitable monomers for preparing poly (ethylene-2,6-naphthalate) and other polymeric materials, commercial-scale operations can, advantageously, use purified 2,6-naphthalene dicarboxylic acid rather than a dialkyl ester. Consider, for example, a polyester manufacturer having equipment and associated processes available for manufacturing polyesters only from an aromatic dicarboxylic acid. In these circumstances, the diester materials would not be suitable and the use of purified 2,6-naphthalene dicarboxylic acid would be required. Additionally, it is advantageous to use 2,6-naphthalene dicarboxylic acid in the manufacture of polyesters because condensation reactions of diacids with glycols to form polyesters do not form an alcohol co-product as do condensation reactions of diesters with a glycol. Polyester manufacturers who use diacids, such as 2,6-naphthalene dicarboxylic acid, do not, therefore, have to provide for sale, recycle, or other use of the alcohol co-product.

In order to prepare high quality polymers most suitable for the aforementioned applications, it is desirable to use purified 2,6-naphthalene dicarboxylic acid. Similarly, it is desirable to use purified forms of other aromatic carboxylic acids when using these compounds for the herein above mentioned applications.

Methods for preparing 2,6-naphthalene dicarboxylic acid include bromine-promoted, metal-catalyzed, liquid-phase oxidation of 2,6-dialkyl naphthalenes. Such processes are disclosed in U.S. Pat. Nos. 3,870,754; 4,950,786 and 4,933,491. Bromine-promoted, metal-catalyzed, liquid-phase oxidation of 2,6-dialkyl naphthalenes, particularly 2,6-dimethyl naphthalene, produces a crude product containing a variety of impurities such as brominated 2,6-naphthalene dicarboxylic acids, 2-formyl-6-naphthoic acid, 2-naphthoic acid and trimellitic acid. These impurities, particularly 2-formyl-6-naphthoic acid, are difficult to remove from crude 2,6-naphthalene dicarboxylic acid. 2,6-Naphthalene dicarboxylic acid must, however, be purified before it can be polymerized to form polymeric materials.

Among the various purification methods for naphthalene dicarboxylic acid which are, at present, in commercial use, one method comprises dissolving a crude naphthalene dicarboxylic acid in an aqueous solution of an alkali, subjecting the solution to treatments, such as, supplemental oxidation, hydrogenation, decoloring by adsorption, etc., and then acidifying the resulting solution with an inorganic acid to obtain the treated naphthalene dicarboxylic acid. However, there are significant problems associated with the use of this type of procedure, due to use of alkali and acid materials in large quantities, which, in turn, leads directly to generation of large quantities of inorganic salt, and, as a result, to production of large quantities of waste water, which must be treated prior to discharge.

Amines have characteristics of a chemical base, and react, for example, with inorganic acid, such as nitrous acid, to give alcohol, nitrogen and water. Polyalkyl amines can also be used to neutralize polycarboxylic acids and form their polyalkyl amine salts. U.S. Pat. No. 2,664,440 to William G. Toland, Jr. described, for example, separation of isophthalic and terephthalic acids from their mixtures. Mixtures of isophthalic acid and terephthalic acid are, according to Toland, first neutralized and converted to their teretiary amine salts which are fractionally crystallized from aqueous solution by adding inorganic ammonium salt, such as ammonium sulfate, to selectively crystallize the terephthalic acid salts. Decomposition of the salts to their corresponding acids is by heating to recover the tertiary amine and acids as decomposition products. The Toland process is, therefore, limited to use of basic tertiary amines capable of forming thermally unstable salts of both the isophthalic acid and the terephthalic acid.

Another available purification method comprises dissolving a crude naphthalene dicarboxylic acid in an organic solvent selected from such high boiling compounds as N,N-dimethylformamide (DMF), N,N-dimethylacetamide (DMAc), and dimethyl sulfoxide (DMSO), treating the solution with activated charcoal, reprecipitation of the naphthalene dicarboxylic acid, and, thereafter, purification by recrystallization of naphthalene dicarboxylic acid. This method has, however, a number of difficulties, such as, for example, drawbacks which are due to the low solubilities of naphthalene dicarboxylic acids in DMF or DMSO, which required the solvent be used in a large amounts. Further, it has been found, that when this method for treating naphthalene dicarboxylic acid is obtained in such a manner as to result in high recovery, almost no improvement is attained in the color of the acid, due, in part, to thermal degradation at temperatures employed. In addition, this method has further problems. DMF and DMSO are difficult to recover because of their high boiling points, and these organic solvents are highly toxic.

Published Japanese patent application A 50 142542 (unexamined) describes a purification method which comprises dissolving crude 2,6-naphthalene dicarboxylic acid in an aqueous solution of a specific alkyl amines (dimethylamine), and then removing the amine from the solution by distillation thereby to precipitate the 2,6-naphthalene dicarboxylic acid. This method has, however, drawbacks which include: (1) amines usable in the method are limited to those which can be easily distilled, because in order to precipitate the naphthalene dicarboxylic acid, the amines should be removed and recovered by distillation; (2) a large proportion of the water in the aqueous solution is lost along with the amine since the amine evaporates as a boiling mixture with water; and (3) the recovery attainable by the method is low because complete removal of the amine from the aqueous solution is impossible.

European Patent Application 0 551 596 A2 describes a method for producing a naphthalene dicarboxylic acid which comprises dissolving a crude naphthalene dicarboxylic acid in non-aqueous mixed solvent consisting of a major amount of an alcohol, e.g. methanol and a minor amount of an amine compound, e.g. triethanol amine, and crystallization of naphthalene dicarboxylic acid from the mixed solvent by cooling. Subsequent washing of the naphthalene dicarboxylic acid crystals with acetic acid was required to achieve purity above 99.0 percent.

Purification of 2,6-naphthalene dicarboxylic acid is considerably more difficult than purification of a dialkyl-2,6-naphthalene dicarboxylate primarily due to low solubility of 2,6-naphthalene dicarboxylic acid in most ordinary solvents, and to its high melting point temperature and low volatility. In aforementioned U.S. Pat. No. 4,933,491, for example, 2,6-naphthalene dicarboxylic acid was purified only after reacting 2,6-naphthalene dicarboxylic acid with a lower alkanoic anhydride to produce a component that is soluble in excess alkanoic anhydride. The "solubilized" 2,6-naphthalene dicarboxylic acid was optionally treated with one or more purification procedures. Xu et al. (Chemistry of Synthetic High Polymers, Vol. 10, pp. 107–11, 1984, Chemical Abstracts CA 102: 185547z) reports that purification of 2,6-naphthalene dicarboxylic acid by sublimation, recrystallization and/or distillation is inefficient and difficult due to the poor solubility and volatility of 2,6-naphthalene dicarboxylic acid and also because the impurities present, having similar properties, adhere to each other.

In contrast, diesters of 2,6-naphthalene dicarboxylic acid are considerably more soluble than 2,6-naphthalene dicarboxylic acid in ordinary organic solvents such as xylenes and methanol, and can be purified in the dissolved state. Furthermore, these diesters, particularly the dimethyl ester, are sufficiently volatile so that they can be purified by distillation. Therefore, one potential method for preparing purified 2,6-naphthalene dicarboxylic acid is to convert a purified dialkyl-2,6-naphthalene dicarboxylate to 2,6-naphthalene dicarboxylic acid by reacting the diester with water to hydrolyze the ester bonds and form the free dicarboxylic acid. One such process is proposed in the aforementioned Xu et al. publication. The process described therein comprises forming purified 2,6-naphthalene dicarboxylic acid by dissolving crude dimethyl-2,6-naphthalene dicarboxylate in a xylene, treating with activated carbon, and then crystallizing purified dimethyl-2,6-naphthalene dicarboxylate. Purified dimethyl-2,6-naphthalene dicarboxylate was subsequently hydrolyzed using a 12 percent potassium hydroxide solution at reflux conditions, and the solution of hydrolyzed ester was acidified with hydrochloric acid to free purified 2,6-naphthalene dicarboxylic acid. While it is reported that this procedure produces high purity 2,6-naphthalene dicarboxylic acid, the procedure described would not be desirable for large-scale production. Use of concentrated base to hydrolyze the ester and the required use of an acid to free the salt of 2,6-naphthalene dicarboxylic acid is not economical on a large scale.

After converting the aromatic carboxylic acid to an ester, the ester can be purified by methods such as recrystallization, distillation, sublimation, etc. The esters are suitably prepared by methods well known in the art. For example, the aromatic carboxylic acid can be heated at an elevated temperature in the presence of an alcohol, and, optionally, in the presence of one or more esterification catalysts. Typically, the alcohol selected is a low-molecular weight alcohol having 1 to about 6 carbon atoms. Methods for preparing the ester 2,6-naphthalene dicarboxylic acid are disclosed in U.S. Pat. No. 4,886,901 to Holzhaurer et al., and in U.S. Pat. No. 5,254,719, the disclosure of which patents are hereby incorporated by reference.

There is, therefore, need for an improved process for preparing relatively pure polycarboxylic acid from typical crude products of liquid phase oxidation, which do not involve intermediate steps of ester formation and hydrolysis. In particular, there is a present need for an integrated process for preparing purified 2,6-naphthalene dicarboxylic acid without formation of any dialkyl-2,6-naphthalene dicarboxylate or require use of any alkanol containing solvent or high boiling organic solvent. The present invention provides such integrated processes.

Other objects and advantages of the invention will become apparent upon reading the following detailed description and appended claims.

SUMMARY OF THE INVENTION

Integrated liquid phase purification processes of the invention comprise, generally, reaction of at least one polyalkyl amine compound in an aqueous solvent with crude solids containing aromatic polycarboxylic acid, such as are formed in liquid phase oxidation a corresponding aromatic compound, to obtain soluble amine salts of the aromatic polycarboxylic acid and impurities retained in the crude solids, precipitation and separation of metal ion impurities, selective extraction and/or adsorption of salts of one or more of the organic impurities from the aqueous solution of the soluble amine salts, acidification of the purified solution with an organic acid to form crystals of the aromatic polycarboxylic acid predominantly without precipitation of the impurities, recovery of purified polycarboxylic acid product from the mother liquor, and, thereafter, distillation of the mother liquor for recovery of amine, higher and/or lower boiling organic acid streams suitable for recycle.

Processes according to this invention are advantageous in that the recovered aromatic polycarboxylic acids are freed of many monofunctional aromatic compounds, difunctional aromatic compounds, trifunctional aromatic compounds, and/or color causing organic compounds formed in a liquid phase oxidation process.

Another element of processes of this invention is that a portion of undesired impurities present with crude aromatic polycarboxylic acid obtained by liquid phase oxidation (impurities consisting of metals, metal oxides, and/or other insoluble materials typically found such crude solids) are easily separated from the solution containing the desired aromatic acid, e.g. in a mechanical filter.

BRIEF DESCRIPTION OF THE DRAWING

The appended claims set forth those novel features which characterize the present invention. The present invention itself, as well as advantages thereof, may best be understood, however, by reference to the following brief description of preferred embodiments taken in conjunction with the annexed drawing, in which:

BRIEF DESCRIPTION OF THE INVENTION

Integrated processes according to the invention are, particularly, suitable for preparation of a purified aromatic polycarboxylic acid obtained by liquid-phase oxidation of a corresponding aromatic compound having at least two oxidizable alkyl or acyl ring substituents or an oxidizable alkyl and acyl ring substituent in non adjacent positions, with a dioxygen-containing gas in a solvent at an elevated temperature and pressure and in the presence of an oxidation catalyst comprising a heavy metal component to prepare crude solids containing the desired aromatic polycarboxylic acid wherein the level of monofunctional, difunctional and/or trifunctional aromatic impurities retained by the crude solids is, typically, in a range downward from about 10 percent, preferably equal to or less than about 5 percent, and more preferably equal to or less than about 3 percent based upon the weight of the crude polycarboxylic acid present.

More particularly, integrated processes for preparation of a purified aromatic polycarboxylic acid obtained by liquid-phase oxidation of a corresponding aromatic compound, comprises, according to the invention, the following: (a) Introducing crude solids containing the desired aromatic polycarboxylic acid into an aqueous solution of a polyalkyl amine containing up to about 20 carbon atoms, preferably up to about 9 carbon atoms, while maintaining the solution at a level of pH in a range upward from about 7 and at temperature and pressure sufficient to maintain the solution substantially in the liquid phase, to form soluble salts of the polycarboxylic acid and one or more of the mono-functional and/or trifunctional aromatic impurities in the aqueous solution. (b) Contacting the aqueous solution with an immiscible liquid solvent or solid adsorbent, transferring a substantial fraction of the salt of at least one of the monofunctional aromatic impurities from the aqueous solution to the immiscible liquid solvent or solid adsorbent, and recovering therefrom purified aqueous solution. (c) Acidifying the purified aqueous solution of the polyalkyl amine salt of the polycarboxylic acid with a carboxylic acid containing from 1 to 6 carbon atoms, preferably containing from 2 to 6 carbon atoms, to a level of pH in a range downward from about 6.7 to form a slurry of precipitated polycarboxylic acid in mother liquor which retains a substantial fraction of the soluble salts of the trifunctional aromatic impurities. And thereafter (d) recovering from the slurry purified polycarboxylic acid product which contains about 2 percent, or less, preferably less than about 1 percent of the monofunctional and/or trifunctional aromatic impurities, and more preferably less than about 0.6 percent, based upon the weight of the polycarboxylic acid present.

Suitable aromatic dicarboxylic acids include aromatic dicarboxylic acids obtained by liquid-phase oxidation of a corresponding aromatic compound having at least two oxidizable alkyl or acyl ring substituents or an oxidizable alkyl and acyl ring substituent in non adjacent positions, with a dioxygen-containing gas in a solvent at an elevated temperature and pressure and in the presence of an oxidation catalyst comprising a heavy metal component to prepare a crude solid. Integrated process of the invention are, advantageously, used to obtain a purified aromatic polycarboxylic acid, selected from the group consisting of terephthalic acid formed by the oxidation of para-xylene, isophthalic acid formed by the oxidation of meta-xylene, 1,5-naphthalene dicarboxylic acid formed by the oxidation of a 1,5-dialkylnaphthalene, 2,7-naphthalene dicarboxylic acid formed by the oxidation of a 2,7-dialkylnaphthalene, and 2,6-naphthalene dicarboxylic acid formed by the oxidation of a 2,6-dialkylnaphthalene. Typically, crude solids containing the desired aromatic polycarboxylic acid also contain levels of monofunctional, difunctional and/or trifunctional aromatic impurities, retained by the crude polycarboxylic acid, equal to as much as about 10 percent, based upon the weight of the crude polycarboxylic acid present, such levels are unsuitable for many commercial uses.

In one aspect of the invention at least a portion of the polyalkyl amine in the aqueous solution used in (a) is, advantageously, derived from the mother liquor subsequent to recovery therefrom of the purified polycarboxylic acid product.

When the desired product is 2,6-naphthalene dicarboxylic acid, the crude solids contain, typically, one or more monofunctional aromatic compound selected from the group consisting of 2-naphthoic acid, 2-methyl-6-naphthoic acid and 2-formyl-6-naphthoic acid and/or trifunctional aromatic compounds, e.g. trimellitic acid.

In one aspect of the integrated process for preparation of a purified aromatic polycarboxylic acid in accordance with the invention step (a) is carried out at temperatures in a range from about 60° F. to about 215° F. and at a pressure sufficient to maintain at least about 80 percent of the polyalkyl amine in the aqueous solution.

In another aspect of the integrated process for preparation of a purified aromatic polycarboxylic acid in accordance with the invention the polyalkyl amine is, preferably, selected from the group consisting of trimethylamine and triethylamine. In another aspect the mother liquor is fractionated as by distillation into at least a first fraction rich in polyalkyl amine and essentially free of carboxylic acid, and another fraction rich in the carboxylic acid and essentially free of polyalkyl amine. In yet another aspect at least a portion of the distillate fraction rich in polyalkyl amine is recycled into the aqueous solution used in (a) and/or at least a portion of the distillate fraction rich in carboxylic acid is recycled into the monocarboxylic acid used in (c).

In another aspect of the invention the contacting of the aqueous solution is, preferably, carried out by passing the solution through at least a first particulate bed comprising active carbon and/or other solid adsorbent, until the active carbon in the first bed is loaded with the salt of at least one of the monofunctional aromatic impurities. The loaded bed is taken out of service and, thereafter, treated to regenerate the active carbon and/or other solid adsorbent for further use by a reconditioning, preferably, by a process which comprises the following: (i) Displacing the aqueous solution containing the polycarboxylic acid from the bed. (ii) Passing an aqueous solution of a polar organic solvent containing from about 1 to about 10 carbon atoms, through the bed to desorb the salts of the impurities. And (iii) flushing the polar organic solvent from the bed with water. Preferred polar organic solvents include alcohols, ethers, esters, and ketones containing from about 1 to about 10 carbon atoms. More preferably, a polar organic solvent selected from the group consisting of alcohols and ketones containing from about 1 to about 4 carbon atoms, and most preferably, tetrahydrofuran.

Acid suitable for acidification of the relatively pure aqueous solution of polycarboxylic acid according to the invention is, preferably, a carboxylic acid selected from a group consisting of formic acid, acetic acid, propionic acid, n-butyric acid, isobutyric acid, n-valeric acid, trimethylacetic acid and caproic acid, and mixtures thereof. More preferably, the carboxylic acid selected from a group consisting of formic acid, acetic acid, propionic acid, and mixtures thereof, and most preferably is acetic acid.

In another aspect the invention is an integrated process for preparation of a purified 2,6-naphthalene dicarboxylic acid obtained by liquid-phase oxidation of a 2,6-dialkylnaphthalene with a dioxygen-containing gas in a solvent at an elevated temperature and pressure and in the presence of an oxidation catalyst comprising a heavy metal component to prepare a crude solid containing the desired purified 2,6-naphthalene dicarboxylic acid wherein the level of monofunctional, difunctional, and/or trifunctional aromatic impurities retained by the crude polycarboxylic acid is equal to or less than about 5 percent, preferably less than about 3 percent based upon the weight of the crude 2,6-naphthalene dicarboxylic acid present. In this preferred embodiment process in accordance with the invention comprise the following: (a) Introducing crude solids containing 2,6-naphthalene dicarboxylic acid into aqueous solution of a trialkyl amine containing up to about 20 carbon atoms, preferably up to about 6 carbon, at temperatures in a range from about 68° F. to about 215° F. and sufficient pressure to maintain at least about 80 percent of the trialkyl amine in the aqueous phase, while maintaining the solution at a level of pH in a range upward from about 7 to form soluble salts of the 2,6-naphthalene dicarboxylic acid and one or more of the monofunctional and/or trifunctional aromatic impurities in the aqueous solution. (b) Contacting the aqueous solution with an immiscible liquid solvent or solid adsorbent, transferring a substantial fraction of the salt of at least one of the monofunctional aromatic impurities from the aqueous solution to the immiscible liquid solvent or solid adsorbent, and recovering therefrom purified aqueous solution. (c) Acidifying the purified aqueous solution of the amine salt of the 2,6-naphthalene dicarboxylic acid with a carboxylic acid containing from 1 to 6 carbon atoms to a level of pH in a range downward from about 6.9 to form a slurry of precipitated 2,6-naphthalene dicarboxylic acid in mother liquor which retains a substantial fraction of the soluble salts of the trifunctional aromatic impurities. And thereafter (d) recovering from the slurry purified 2,6-naphthalene dicarboxylic acid product which contains 1 percent, or less, of the monofunctional and/or trifunctional aromatic impurities, based upon the weight of the 2,6-naphthalene dicarboxylic acid present.

In a preferred embodiment of the invention (a) is carried out at temperatures in a range from about 68° F. to about 175° F. and sufficient pressure to maintain at least about 80 percent of the trialkyl amine in the aqueous solution.

In a preferred embodiment of the integrated process for preparation of a purified 2,6-naphthalene dicarboxylic acid in accordance with the invention the distillate fraction rich in the trialkyl amine is, predominantly, recycled into the aqueous solution used in step (a), and wherein the fraction rich in the carboxylic acid is, predominantly, recycled with the carboxylic acid used in (c).

In another preferred embodiment of the invention (c) is carried out to a level of pH in a range from about 6.7 to about 5.0 using a carboxylic acid selected from a group consisting of acetic acid, propionic acid, and mixtures thereof, thereby resulting in retention of undesired impurities in the mother liquor.

In yet another preferred embodiment of the invention the trialkyl amine is selected from the group consisting of trimethylamine and triethylamine, wherein pH of the aqueous solution is reduced in (c) to a level of pH in a range from about 6.7 to about 5.0 by admixing with acetic acid, and wherein the purified 2,6-naphthalene dicarboxylic acid has color measurements of L*-values in a range upward from about 91 to about 99, and b*-values in a range downward from about 10 to about of 3.

In one aspect of the integrated process for preparation of a purified 2,6-naphthalene dicarboxylic acid in accordance the invention the process further comprises; (e) fractionating at least portion of the mother liquor by distillation subsequent to recovery therefrom of the purified polycarboxylic acid product to recover at least a first aqueous fraction rich in the trialkyl amine which first fraction contains, generally, less than 10 percent, preferably less than about 5 percent, and more preferably less than about 1 percent of the carboxylic acid, and another aqueous fraction rich in the carboxylic acid which other fraction contains less trialkyl amine than the mother liquor. Preferably fraction rich in the carboxylic acid contains less than about 10 percent trialkyl amine, and more preferably less than about 5 percent.

In a preferred embodiment the integrated process for preparation of a purified 2,6-naphthalene dicarboxylic acid in accordance with the invention the distillate aqueous fraction rich in the trialkyl amine is, predominantly, recycled into the aqueous solution used in (a), and wherein the distillate aqueous fraction rich in the carboxylic acid is, predominantly, recycled with the carboxylic acid used in (c).

In another aspect the invention is an integrated process for preparation of a purified 2,6-naphthalene dicarboxylic acid obtained by liquid-phase oxidation of a 2,6-dialkylnaphthalene with a dioxygen-containing gas in an acetic acid containing solvent at an elevated temperature and pressure and in the presence of an oxidation catalyst comprising a heavy metal component to prepare crude solids containing the desired purified 2,6-naphthalene dicarboxylic acid wherein the level of monofunctional and/or trifunctional aromatic impurities retained by the crude solids is equal to or less than about 3 percent based upon the weight of the crude 2,6-naphthalene dicarboxylic acid present, which process comprises: (a) Introducing crude solids containing 2,6-naphthalene dicarboxylic acid and one or more of the monofunctional and/or trifunctional aromatic impurities, into aqueous solution of a trialkyl amine selected from the group consisting of trimethylamine and triethyl amine at temperatures in a range from about 68° F. to about 175° F. and sufficient pressure to maintain at least about 80 percent of the trialkyl amine in the aqueous, while maintaining the solution at a level of pH in a range upward from about 7, to form soluble salts of the 2,6-naphthalene dicarboxylic acid and one or more of the monofunctional and/or trifunctional aromatic impurities in the aqueous solution. (b) Contacting the aqueous solution with bed of particulate adsorbent comprising active carbon, transferring a substantial fraction of the salt of at least one of the monofunctional aromatic impurities from the aqueous solution to the bed, and recovering therefrom purified aqueous solution. (c) Heating the purified aqueous solution of the amine salt of the 2,6-naphthalene dicarboxylic acid to elevated temperatures in a range upward from about 70° C. to form a slurry of precipitated 2,6-naphthalene dicarboxylic acid in mother liquor which retains a substantial fraction of the soluble salts of the trifunctional aromatic impurities. (d) Recovering from the slurry purified 2,6-naphthalene dicarboxylic acid product which contains 1 percent, or less, of the monofunctional and/or trifunctional aromatic impurities, based upon the weight of the 2,6-naphthalene dicarboxylic acid present. (e) And optionally, fractionating at least portion of the mother liquor by distillation subsequent to recovery therefrom of the purified polycarboxylic acid product to recover at least a first aqueous fraction rich in the trialkyl amine which first fraction contains less than 1 percent acetic acid, and another aqueous fraction rich in the acetic acid which fraction contains less than 5 percent trialkyl amine. Preferably the fraction rich in the trialkyl amine is, predominantly, recycled into the aqueous solution used in (a), and wherein the fraction rich in the acetic acid is, predominantly, recycled with the acetic acid used in (c).

In yet another aspect the invention is an integrated process for for preparation of a purified 2,6-naphthalene dicarboxylic acid obtained by liquid-phase oxidation of a 2,6-dialkylnaphthalene with a dioxygen-containing gas in a solvent at an elevated temperature and pressure and in the presence of an oxidation catalyst comprising a heavy metal component to prepare crude solids containing the desired purified 2,6-naphthalene dicarboxylic acid wherein the level of monofunctional, difunctional and/or trifunctional aromatic impurities retained by the crude solids is equal to or less than about 3 percent, based upon the weight of the crude 2,6-naphthalene dicarboxylic acid present, which process comprises: (a) introducing crude solids containing 2,6-naphthalene dicarboxylic acid into aqueous solution of a trialkyl amine containing up to about 20 carbon atoms at temperatures in a range from about 68° F. to about 215° F. and sufficient pressure to maintain at least about 80 percent of the trialkyl amine in the aqueous, while maintaining the solution at a level of pH in a range upward from about 7 to form soluble salts of the 2,6-naphthalene dicarboxylic acid and one or more of the monofunctional and/or trifunctional aromatic impurities in the aqueous solution; (b) passing the aqueous solution through at least a first particulate bed of adsorbent comprising active carbon, transferring a substantial fraction of the salt of at least one of the monofunctional aromatic impurities from the aqueous solution to the immiscible liquid solvent or solid adsorbent, and recovering therefrom purified aqueous solution; until the active carbon in the first bed is loaded with the salt of at least one of the monofunctional aromatic impurities; thereafter, (c) treating the loaded bed to regenerate the active carbon and/or other solid adsorbent for further use by a reconditioning process which comprises; (i) displacing the aqueous solution containing the polycarboxylic acid from the bed, (ii) passing an aqueous solution of a polar organic solvent containing from about 1 to about 10 carbon atoms, through the bed to desorb the salts of the impurities, and (iii) flushing the polar organic solvent from the bed with water; and (d) repeating step (b-11)

In a preferred embodiment the integrated process for preparation of a purified 2,6-naphthalene dicarboxylic acid in accordance with the invention further comprises; (e)acidifying the purified aqueous solution of the amine salt of the 2,6-naphthalene dicarboxylic acid with a carboxylic acid containing from 1 to 6 carbon atoms to a level of pH in a range downward from about 6.9 to form a slurry of precipitated 2,6-naphthalene dicarboxylic acid in mother liquor which retains a substantial fraction of the soluble salts of the trifunctional aromatic impurities, and (f) recovering from the slurry purified 2,6-naphthalene dicarboxylic acid product which contains less than about 1 percent of the monofunctional and/or trifunctional aromatic impurities, based upon the weight of the 2,6-naphthalene dicarboxylic acid present.

Advantageously, 2,6-naphthalene dicarboxylic acid purified in accordance with the invention has an optical density in a range from about 0 to about 5, an ash content of less 500 ppm, and/or a metals content of less than 200 ppm.

DETAILED DESCRIPTION OF THE INVENTION

Carboxyl groups in preferred aromatic acids are either attached directly to an independent benzene ring or to benzene rings of a condensed ring system such as naphthalene, in which two benzene rings have two carbon atoms in common or anthracene in which three rings are similarly connected so that the rings are not independent.

Aromatic polycarboxylic acids, particularly terephthalic acid and 2,6-naphthalene dicarboxylic acid, are conveniently prepared by the liquid phase, metal catalyzed oxidation of an alkyl or acyl substituted aromatic compound. During this oxidation, an alkyl group (for example a methyl, ethyl or isopropyl group) or acyl group is oxidized to a carboxylic acid group. Although this is an effective oxidation reaction, it nevertheless has some drawbacks. For example, when a 2-alkyl or 2-acyl substituted naphthalene compound is oxidized, the naphthalene ring itself is subject to oxidation and trimellitic acid is produced. Incomplete oxidation of a methyl group produces an aldehyde group instead of a carboxylic acid group. Furthermore, when a promoter such as bromine is used during the liquid phase oxidation, brominated aromatic carboxylic acids are produced. Although all of these impurities are deleterious and therefore undesirable, trimellitic acid is particularly troublesome because it tends to complex tightly to the metal oxidation catalysts. Such complexed metal is difficult to remove from the desired aromatic polycarboxylic acids. Thus, a method that provides for an aromatic polycarboxylic acid having a reduced level of trimellitic acid and/or other impurities, is desirable. The present invention provides such a method.

Methods for conducting the liquid phase, heavy metal catalyzed oxidation of an alkyl- or acyl-substituted aromatic compound to their corresponding aromatic carboxylic acid are well known in the art. For example, U.S. Pat. Nos. 4,950,786, 4,933,491; 3,870,754 and 2,833,816 disclose such oxidation methods. Suitable heavy metal oxidation catalysts include, typically, those metals having an atomic number of about 21 to about 82, inclusive, preferably a mixture of cobalt and manganese. Preferred oxidation solvents contain a low molecular weight carboxylic acid having 2 to about 6 carbon atoms, inclusive, preferably it is acetic acid or mixtures of acetic acid and water. Reaction temperatures in a range from of about 300° F. to about 450° F. are typical, and reaction pressures are such that the reaction mixture is under liquid phase conditions. A promoter such as a low molecular weight ketone having 2 to about 6 carbon atoms or a low molecular weight aldehyde having 1 to about 6 carbon atoms can also be used. Bromine promoter compounds known in the art such as hydrogen bromide, molecular bromine, sodium bromide and the like can also be used. A source of dioxygen is also required, and it is, typically, compressed air.

A particularly suitable method for oxidizing a 2,6-dialkyl or 2-acyl-6-alkylnaphthalene to 2,6-naphthalene dicarboxilic acid is disclosed in commonly assigned U.S. Pat. No. 4,933,491 to Albertins et al. Suitable solvents for such liquid phase oxidation of 2,6-dialkyl or 2-acyl-6-alkylnaphthalene include benzoic acid any aliphatic carboxylic acid having from 2 to about 6 carbon atoms. Preferred solvents contain at least one monocarboxylic acid selected from the group consisting of acetic acid, propionic acid, n-butyric acid, isobutyric acid, n-valeric acid trimethylacetic acid, caproic acid, and water. More preferably the solvent is a mixture of water and acetic acid, which mixture is preferably 1 to 20 weight percent water. The source of dioxygen employed in such liquid phase oxidation of a of 2,6-dialkyl or 2-acyl-6-alkylnaphthalene can vary in dioxygen content from that of air to pure molecular oxygen gas. Because of economy, compressed air is a preferred source of dioxygen.

Catalyst systems employed in such oxidation of 2,6-dialkyl or 2-acyl-6-alkylnaphthalene comprise a bromine-containing compound and at least one of a cobalt- and manganese-containing compound. Preferably, the catalyst comprises cobalt-, manganese-, and bromine-containing components.

In operation, the minimum pressure at which the oxidation reactor is maintained is that pressure which will maintain a substantial liquid phase of the 2,6-dialkyl or 2-acyl-6-alkylnaphthalene and at least 70 weight percent of the solvent. The 2,6-dialkyl or 2-acyl-6-alkylnaphthalene and solvent not in the liquid phase because of vaporization is removed from the oxidation reactor as a vapor-gas mixture, condensed and then returned to the oxidation reactor. When the solvent is an acetic acid-water mixture, suitable reaction gauge pressures in the oxidation reactor are in the range of from from about 0 kg/cm2 to about 35 kg/cm2, and typically are in the range of from about 10 kg/cm2 to about 30 kg/cm2. The temperature range within the oxidation reactor is, generally, from about 250° F., preferably from about 350° F. to about 450° F., preferably to about 420° F. At temperatures greater than 450° F., excessive burning of the solvent and/or naphthalene compound occurs. The solvent residence time in the oxidation reactor is, generally from about 20 to about 150 minutes and preferably from about 20 to about 120 minutes.

Depending on the oxidation reaction conditions used, the aromatic feed compound selected, the oxidation catalysts, and the levels of catalyst selected, the reaction mixture produced in the oxidation reaction contains, in addition to the desired aromatic carboxylic acid, a number of impurities and reaction by-products. For example, when 2,6-dimethyl naphthalene is the aromatic feed compound for the oxidation reaction and a catalyst comprising cobalt, manganese and bromine components is used, the oxidation reaction mixture directly from the oxidation reactor, (also called the total reactor effluent or TRE) contains the reaction solvent, which is typically a mixture of acetic acid and water, the desired 2,6-naphthalene dicarboxylic acid, and impurities including trimellitic acid (TMLA), bromo-2,6-naphthalene dicarboxylic acid (BR-2,6-NDA), 2-formyl-6-naphthoic acid (2-FNA), 2-naphthoic acid (2-NA), a collection of other impurities, and cobalt and manganese catalyst components. Acetic acid and water can be removed by evaporation or distillation from the oxidation reaction mixture to leave a residue of solids. Analysis of these solids provides a useful assessment of all of the solid components in the oxidation reaction mixture and consequently an assessment of the yield of desired product and reaction by-products. In a typical oxidation of 2,6-dimethyl naphthalene, the amount of trimellitic acid in the oxidation reaction mixture solids can be as high as 5 percent by weight of the solids and typically about 3 to about 4 percent. The amount of 2-formyl-6-naphthoic acid can be as high as 1 percent and typically is about 0.4 to about 0.5 percent by weight of the solids. The amount of bromo-2,6-naphthalene dicarboxylic acids can be as high as 3 percent and is typically about 0.2 to 1 percent by weight of the solids. The total of cobalt and manganese in the solid portion of the oxidation reaction mixture can be as high as 4 wt percent.

Although the 2,6-naphthalene dicarboxylic acid is generally insoluble in the oxidation reaction mixture, particularly when the oxidation reaction mixture is cooled to a temperature below the oxidation reaction temperature, and can be easily separated from the oxidation reaction mixture, the 2,6-naphthalene dicarboxylic acid recovered is also contaminated with trimellitic acid, 2-formyl-6-naphthoic acid, bromo-2,6-naphthalene dicarboxylic acids, other organic impurities and by-products as well as the cobalt and manganese oxidation metal catalysts. Furthermore, even when the 2,6-naphthalene dicarboxylic acid is separated from the oxidation mixture at an elevated temperature and even if the separated 2,6-naphthalene dicarboxylic acid is washed with fresh solvent at an elevated temperature to remove residual mother liquor, the recovered 2,6-naphthalene dicarboxylic acid still contains substantial amounts of the aforementioned impurities and byproducts which require removal from the 2,6-naphthalene dicarboxylic acid.

As mentioned herein above, the aromatic polycarboxylic acid recovered from the oxidation reaction mixture is admixed with aqueous solution of a polyalkyl amine to form relatively soluble salts and obtaining an aqueous solution thereof. Amines are, as is well known, derivatives of ammonia (NH3) in which one, two, or three hydrogen atoms are replaced by organic moieties, in particular by alkyl groups. Polyalkyl amine amines are compounds in which two or three hydrogen atoms of ammonia replaced with the same or different alkyl groups. Polyalkyl amine amines are known as secondary amines, named as dialkyl amines and tertiary amines, named as trialkyl amines, i.e. dimethylamine, methylethylamine, di-n-propylamine, or n-propylisopropylamine and trimethylamine, dimethylethylamine, or methylethyl-n-propylamine, etc.

Processes according to the invention can, advantageously, be carried out using more than one, preferably at least two, independent carbon beds for continuous operation are provided To allow use of shorter times between carbon regenerations in continuous operation, at least three independent carbon beds are, preferably, provided and each bed is, typically, designed to be used for a single operating shift (8 hours) before regeneration.

Regeneration of each independent bed is, preferably, performed in three steps. For example, at the end of each eight hour 2,6-naphthalene dicarboxylic acid impurity adsorption cycle, the flow of process feed into one bed is stopped and aqueous Polyalkyl amine amines passed through the bed to flush out the solution of amine salts of 2,6-naphthalene dicarboxylic acid feedstock. Aqueous polyalkyl amine having the same concentration of polyalkyl amine used to form the salt solution is advantageously used (from the same tank that is used to provide polyalkyl amine to the 2,6-naphthalene dicarboxylic acid reactor). Adsorbed impurities are retained on the carbon. While a solution having a different concentration of polyalkyl amine can be used for this first regeneration step, it is preferred to use the same concentration so the flush materials can be directly recombined with fresh feedstock without any further processing cost. Use of a different solution would require an additional storage tank, two additional agitated vessels, and the material could not be directly recycled with the fresh feed, but would require additional processing.

In the second step of carbon regeneration, a one-to-one tetrahydrofuran (THF)/water mixture is used to desorb the 2,6-naphthalene dicarboxylic acid impurities. Effluent from the bed during the second set of carbon regeneration, (2,6-naphthalene dicarboxylic acid impurity desorption), is, advantageously, fed to a surpressed vaporization heat exchanger recirculation loop and flash drum for solvent recovery. Solids from the flash drum are purged from the unit to disposal, for example in an incinerator, while vapor is condensed and recombined with the fresh THF/water stream. Desorption of 2,6-naphthalene dicarboxylic acid impurities is, typically, continued for about one-half of the regeneration cycle, i.e., about four hours.

In the third step of the carbon regeneration, fresh water is used to remove the tetrahydrofuran from the bed. Fresh water is passed through the bed (2 bed volumes), and the effluent water/tetrahydrofuran mixture is sent to a distillation tower that separates the mixture into a 50 wt. % tetrahydrofuran/50 wt. % water overhead mixture for recycle to carbon regeneration step 2, and a bottoms stream for disposal.

Use of a distillation unit to "break" the acetic acid/trimethyl amine complex while simultaneously separating out excess water, is a critical element of the present invention. Operating the tower with water rich liquid mixture on trays allows, preferably, recycle of the carboxylic acid and amines within the process. Removal of water gives, advantageously, operating flexibility.

Steps of this invention can be carried out in a batch mode as well as a continuous mode. For commercial scale purification of terephthalic acid and 2,6-naphthalene dicarboxylic acid continuous modes are preferred. In any event, however, L*-values, a*-values, and/or of b*-values are monitored so as to obtain a desired color level of final product.

Color levels of crude aromatic polycarboxylic acid and purified acid product can be monitored or evaluated directly or indirectly, as described herein below.

In one aspect, color level of crude aromatic polycarboxylic acid and purified aromatic polycarboxylic acid product can be ascertained by measuring its b*-value on the Hunter Color Scale as described in Hunter, The Measurement of Appearance, Chapter 8, pp. 103 to 132, John Wiley & Sons, NY. (1975), and in Wyszecki et al., Color Science Concepts and Methods, Quantitative Data and Formulae, 2d Ed., pp. 166 to 168, John Wiley & Sons, NY.(1982).

More specifically, b*-values of crude aromatic polycarboxylic acid and purified aromatic polycarboxylic acid product can be determined using, for example, a Diano Match Scan Spectrophotometer as follows. A sample of solid product is pressed into a pellet having a thickness of about 0.25 inch and a diameter of about 1 inch. The pellet is then irradiated with white light that has been UV-filtered. The spectrum of visible light reflected from the sample is determined and tristimulus values (X Y, and Z) are computed using the CIE Standard Observer functions. Using a weighted-ordinate method, tristimulus values are obtained from the following equations:

$$X = \sum_{400}^{700} R\lambda\, x\lambda, \qquad Y = \sum_{400}^{700} R\lambda\, y\lambda, \qquad Z = \sum_{400}^{700} R\lambda\, z\lambda,$$

where $R\lambda$ is the percent reflectance of the pellet at wavelength $\lambda$ and $x\lambda$, $y\lambda$, and $z\lambda$ are Standard Observer functions at wavelength l for CIE Illuminated D65. Tristimulus values X, Y, and Z, identify the color of the pellet in terms of a mixture of primary colors that match it visually. Tristimulus values, however, are of limited use as color specifications, because they do not correlate with visually meaningful attributes of color appearance and are not uniform in the spacing of colors as related to visual differences. As a result, "Uniform Color Scales" (UCS) have been adopted which use simple equations to approximate visual response. The UCS scale used by the Diano instrument is the CE 1976 L*a*b* formula which converts tristimulus values to L*, a*, and b* values as shown below:

$$L^* = 25(100\, Y/Y_0)^{1/3} - 16$$

$$a^* = 500[(X/X_0)^{1/3} - (Y/Y_0)^{1/3}]$$

$$b^* = 500[(Y/Y_0)^{1/3} - (Z/Z_0)^{1/3}]$$

The L* value is a measure of the luminosity or whiteness of an object where a L* value of 100 is pure white, a L* value of 0 is black, and values in a range 0<L* <100 are gray. The L* value is strictly a function of tristimulus Y-value. The b*-value is a measure of a yellowness-blueness attribute where positive b*-values represent yellow appearance and negative b*-values represent blue appearance. The b*-value is a function of both tristimulus values Y and Z

PREFERRED EMBODIMENTS OF THE INVENTION

While this invention is susceptible of embodiment in many different forms, this specification and accompanying drawing disclose only some specific forms as an example of the use of the invention. In particular, preferred embodiments of the invention for preparing relatively pure 2,6-naphthalene dicarboxylic acid from a catalytic liquid phase oxidation process using compressed air are illustrated and described. The invention is not intended to be limited to the embodiments so described, and the scope of the invention will be pointed out in the appended claims.

The apparatus of this invention is used with certain conventional components the details of which, although not fully illustrated or described, will be apparent to those having skill in the art and an understanding of the necessary function of such components.

Figure 1:
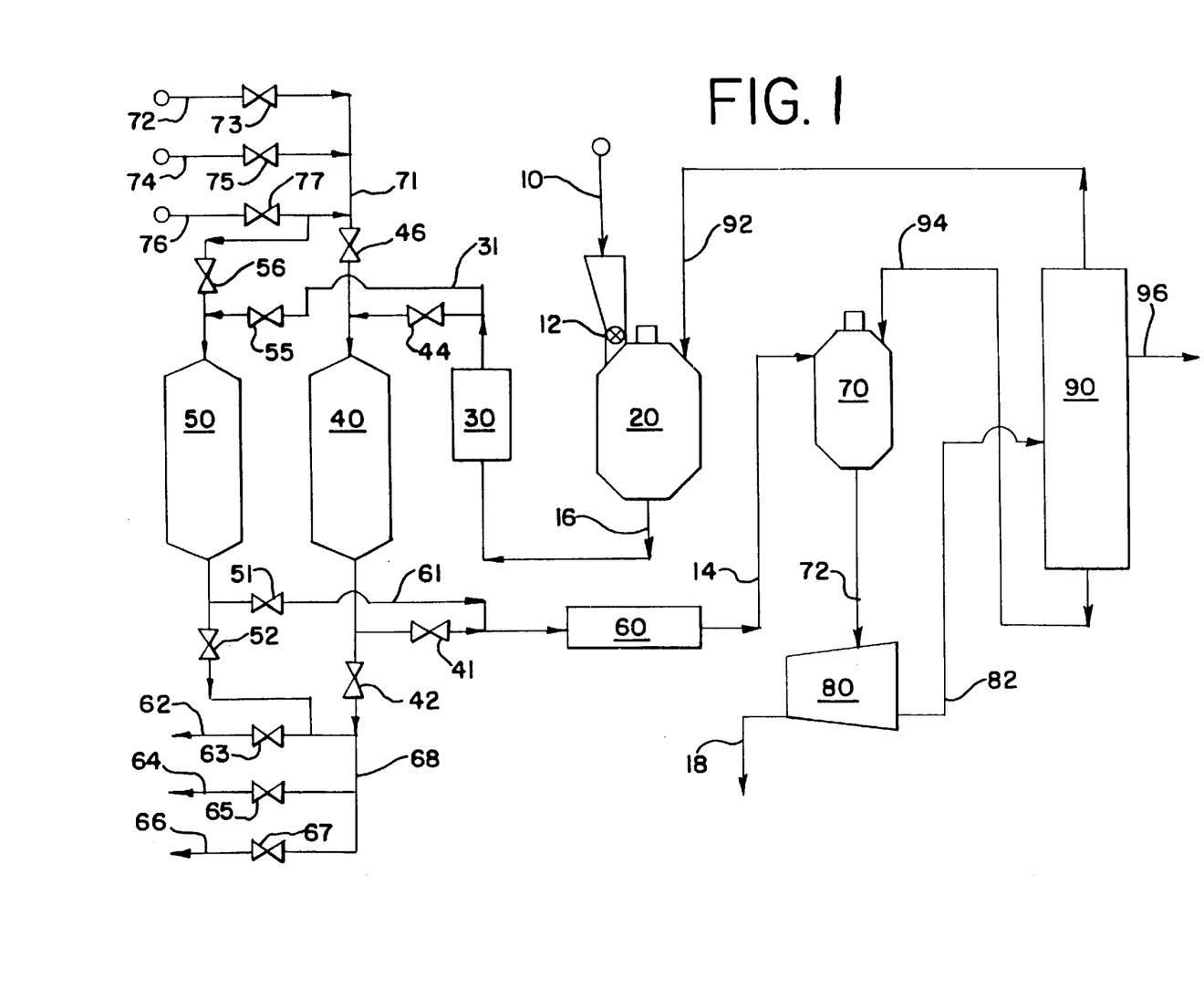
FIG. 1 is a schematic diagram of a preferred method for operating the process of this invention in the continuous mode being arranged to provide sufficient reactants for the reactions and to maintain suitable reaction temperatures in accordance with the present invention.

More specifically with reference to FIG. 1, the integrated liquid phase purification system comprises: one or more agitated vessels for reaction of an amine with crude 2,6-naphthalene dicarboxylic acid, illustrated as amine reaction vessel 20; adsorption vessels containing beds of a suitable solid adsorbent, illustrated as vessels 40 and 50; acidification vessels for precipitation of 2,6-naphthalene dicarboxylic acid, illustrated as mechanically agitated vessel 70; solids recovery apparatus, illustrated as centrifugal filter 80; and distillation units for recovery of amine and aliphatic acid streams suitable for recycle, illustrated as separation tower 90.

During operation of the integrated liquid phase purification system, crude 2,6-naphthalene dicarboxylic acid, for example in granular form, from a catalytic liquid phase oxidation process using compressed air, is fed from an intermediate storage (not shown) through metering conveyor 10 and rotary valve 12 into amine reaction vessel 20. A recycle stream of water and trimethyl amine is fed, through conduit 92, into amine reaction vessel 20 to dissolve the crude 2,6-naphthalene dicarboxylic acid and form a solution of the resulting salt. Amine reaction vessel 20 is, typically, provided with jacketing (not shown) to remove any exothermic heat of dissolution and control the temperature of the resulting salt solution.

Weight ratio of water to trimethyl amine in the amine recycle stream is, advantageously, in a range upward from about 1, i.e., at least 50 weight percent water, preferably, in a range upward from about 2. More preferably amine recycle streams contain from about 70 percent to about 90 percent water and from about 30 percent to about 10 percent trimethyl amine by weight. Most preferably, amine recycle streams contain from about 75 percent to about 85 percent water and from about 25 percent to about 15 percent trimethyl amine by weight. Feed rates into amine reaction vessel 20 are, generally, controlled so as to provide an effluent therefrom which contains at least about 50 percent water by weight, preferably from about 50 percent to about 70 percent by weight.

Effluent from amine reaction vessel 20 flows through mechanical filter 30, manifold 31 and, alternately, through valve 44 or valve 55 into one of two adsorption vessels 40 and 50 which contain beds of a suitable solid adsorbent, such as activated carbon.

Effluent from adsorption vessels 40 and 50 flows through valve 51 or valve 41, manifold 61, mechanical filter 60, to remove any traces of tramp carbon that may have been picked up from the carbon beds, and conduit 14, into mechanically agitated vessel 70. A recycle stream of water and acetic acid is fed, through conduit 94, into vessel 70 to precipitate purified 2,6-naphthalene dicarboxylic acid crystals and form a complex of acetic with amine in an aqueous mother liquor. Reaction vessel 70 is, typically, provided with jacketing (not shown) to remove any exothermic heat of acidification and control the temperature of the resulting mixture.

The effluent mixture from reaction vessel 70 is fed through conduit 72 into centrifugal filter 80 to separate mother liquor from 2,6-naphthalene dicarboxylic acid crystals, which wet acid crystals are transferred from centrifuge 80 into a dryer (not shown) through conveyor 18. Mother liquor flows from centrifuge 80 through conduit 82 into separation tower 90.

Separation of mother liquor by distillation in tower 90 according to this invention breaks the acetic acid/amine complex, while simultaneously separating out excess water through a sidedraw and conduit 96 to water treatment unit (not shown). This allows, advantageously, economical recycle of acetic acid and trimethyl amine within the integrated process. Removal of water gives additional operating flexibility.

Critical elements of distillation in accordance with this invention include operating with water rich liquid mixtures in the tower, and controlling the separation to provide suitable aqueous recycle streams within the process for purification of 2,6-naphthalene dicarboxylic acid by amines. Distillation of the mother liquor in accordance with the invention is, advantageously, controlled to provide a liquid recycle stream from the top of the tower containing about 20 percent to about 30 percent trimethyl amine and about 80 percent to about 70 percent water based upon the weight of the liquid recycle stream. Amounts of trimethyl amine in uncondensed vapor are less than about 10 percent based upon weight of recovered trimethyl amine, preferably less than about 5 percent, and more preferably less than about 1 weight percent. Trimethyl amine in the water side-draw going to the water treatment unit amounts, preferably, to less than about 10 percent based upon weight of recovered trimethyl amine, more preferably less than about 5 weight percent. During continuous operation of the distillation at about atmospheric pressure, temperatures at the bottom of tower 90 are, preferable in a range from about 200° F. to about 240° F., and temperatures at the top are, preferable in a range from about 150° F. to about 190° F.

During continuous operation of this embodiment, the time required for regeneration, alternately, of spent carbon beds, is provided by using two (as shown) or three independent adsorption vessels containing the carbon beds. Regenerations are, advantageously, performed according to this invention in three steps.

At the end of each bed's adsorption cycle, the adsorption vessel which contains the spent bed, for example vessel 50, is isolated from the process flow by means of valve 51 and valve 55. During the first stage of regeneration a first regeneration stream containing water and trimethyl amine is fed, from a storage tank (not shown) through conduit 72, valve 73, manifold 71 and valve 56 into vessel 50, to remove adsorbed impurities form the crude 2,6-naphthalene dicarboxylic acid to form a solution containing, for example, 8 percent 2,6-naphthalene dicarboxylic acid, 18 percent trimethyl amine, and 74 percent water. This effluent solution flows from vessel 50 though valve 52, manifold 68, valve 63, and conduit 62 to a suitable trimethyl amine recovery unit. Trimethyl amine content of the first regeneration stream is at least about 2 percent trimethyl amine by weight. First regeneration streams contain, preferably, from about 70 percent to about 98 percent water and from about 30 percent to about 2 percent trimethyl amine by weight. More preferably, first regeneration streams contain from about 75 percent to about 85 percent water and from about 25 percent to about 15 percent trimethyl amine by weight. First regeneration streams have advantageously, the same composition as the amine recycle stream, so this material can be directly recombined with fresh feedstock without any further processing cost.

During the second stage of regeneration a second regeneration stream containing water and tetrahydrofuran is fed, from a storage tank (not shown) through conduit 74, valve 75, manifold 71 and valve 56 into vessel 50, to remove adsorbed impurities from the crude 2,6-naphthalene dicarboxylic acid to form a solution containing, for example, 0.5 percent 6-formyl-2-naphthoic acid, 3 percent 2,6-naphthalene dicarboxylic acid, 48 percent water and 48 percent tetrahydrofuran. Effluent solution from the second stage of regeneration flows from vessel 50 though valve 52, manifold 68, valve 65, and conduit 64 to a tetrahydrofuran recovery unit.

In a preferred embodiment of this invention, the tetrahydrofuran recovery unit comprises a surpressed vaporization heat exchanger recirculation loop and flash drum for solvent recovery. Solids from the flash drum are sent to an incinerator, while vapor is condensed and recombined with the fresh tetrahydrofuran and water to form a suitable second regeneration stream, which contains, preferably, about 50 percent tetrahydrofuran by weight.

During the third stage of regeneration fresh water is fed, through conduit 76, valve 77, manifold 71 and valve 56 into vessel 50, to remove tetrahydrofuran. Effluent solution from the third stage of regeneration flows from vessel 50 though valve 52, manifold 68, valve 67, and conduit 66 to a distillation tower that separates the mixture into a 50 wt. % tetrahydrofuran/50 wt. % water overhead mixture for recycle to carbon regeneration step 2, and a bottoms stream for disposal.

Operating under conditions wherein substantially all of the 2,6-naphthalene dicarboxylic acid produced is solubilized is also advantageous, particularly when using a baffled, plug flow-type reactor or other type of baffled reactor, because plugging problems are eliminated. Whereas, when operating under conditions where a portion of the 2,6-naphthalene dicarboxylic acid is not in solution, the resulting slurry of 2,6-naphthalene dicarboxylic acid in the reactor and piping could lead to plugging.

Following acidification, the mother liquor is, optionally, cooled to further crystallize 2,6-naphthalene dicarboxylic acid. When operating under conditions where substantially all of the 2,6-naphthalene dicarboxylic acid is in solution, this cooling step is advantageous to recover the 2,6-naphthalene dicarboxylic acid by crystallizing more of the dissolved 2,6-naphthalene dicarboxylic acid. Preferably, the mother liquor is cooled to a temperature below about 400° F., more preferably below about 250° F. The rate of cooling affects particle size of the 2,6-naphthalene dicarboxylic acid produced. It is preferable to cool the reaction mixture at a rate that promotes the formation of large particle size 2,6-naphthalene dicarboxylic acid. Cooling rates of less than about 50° F. per minute, preferably less than about 40° F per minute and most preferably less than about 10° F. per minute provide for large particle size 2,6-naphthalene dicarboxylic acid.

Following the optional cooling step, the 2,6-naphthalene dicarboxylic acid is recovered by partitioning the 2,6-naphthalene dicarboxylic acid from residual water using a suitable means for partitioning a solid phase component from a liquid phase component. For example, solid 2,6-naphthalene dicarboxylic acid can be partitioned from the water phase by filtration, centrifugation, settling, and the like. In this partitioning or separation process the large particle size 2,6-naphthalene dicarboxylic acid produced by the process of this invention is advantageous in that large particles do not "blind" filters and plug centrifuge baskets as readily as fine particles, or retain as much mother liquor, thereby making the partitioning process considerably more efficient. It is desirable to partition the 2,6-naphthalene dicarboxylic acid from the water at an elevated temperature, preferably at a temperature of at least about 150° F., and more preferably at a temperature of at least about 200° F. Filtration at these temperatures provides for a purer 2,6-naphthalene dicarboxylic acid.

After the 2,6-naphthalene dicarboxylic acid is partitioned from the aqueous mother liquor, it is preferably washed with a suitable solvent such as water, a low molecular weight carboxylic acid, e.g. acetic acid, or an aromatic hydrocarbon such as toluene, xylene, etc. Water is the preferred solvent for washing the 2,6-naphthalene dicarboxylic acid. A suitable amount of solvent to wash the 2,6-naphthalene dicarboxylic acid is an amount such that the weight ratio of solvent to 2,6-naphthalene dicarboxylic acid is at least about 1:1, and preferably at least about 2:1, respectively. It is also preferable to conduct the washing step at an elevated temperature. For example, when water is the solvent for the washing step, it is advantageous for the water to be at a temperature of at least about 150° F. Preferably the water should be at a temperature in the range of about 150° F. to about 210° F. Due to the solubility of 2,6-naphthalene dicarboxylic acid in water, the amount of water used to wash the 2,6-naphthalene dicarboxylic acid preferably should not be an amount that will dissolve more than about 10 weight percent of the 2,6-naphthalene dicarboxylic acid being washed. Otherwise, the losses of 2,6-naphthalene dicarboxylic acid will be too great.

EXAMPLES OF THE INVENTION

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

Example 1

This example demonstrates preparation of purified 2,6-naphthalene dicarboxylic acid from crude solids obtained by liquid-phase oxidation of a 2,6-dialkylnaphthalene with a dioxygen-containing gas in a solvent at an elevated temperature and pressure and in the presence of an oxidation catalyst comprising a heavy metal component. Purification of the crude solids was by (a) introducing crude solids into an aqueous solution of trimethylamine; (b) contacting the aqueous solution with activated carbon, and recovering therefrom purified aqueous solution; (c) acidifying the purified aqueous solution with acetic acid, and (d) recovering from the slurry purified 2,6-naphthalene dicarboxylic acid polycarboxylic acid product which contained less than 1000 ppmw of mono-functional and/or trifunctional aromatic impurities, based upon the weight of the polycarboxylic acid present.

Analysis of a crude 2,6-naphthalene dicarboxylic acid feedstock is given in Table 1 as sample NDA-1. This feedstock contains several impurities that are undesirable when the 2,6-naphthalene dicarboxylic acid (2,6-NDA) is used as a monomer for polyethylene naphthalate including naphthalene triacids (NTA), 6-formyl-2-naphthoic acid (6FNA), and 2-methyl-6-naphthoic acid (MNA). Monocarboxylic acids, 0.153 percent in sample NDA-1, are undesirable because they may limit the molecular weight during subsequent polymerization and the 6FNA may contribute to color.

Solid crude 2,6-NDA (600 g, composition listed as NDA-1 in Table 1) was mixed with water (2344 g) and trimethylamine (TMEA, 456 g) to yield an aqueous solution containing 18.2 percent 2,6-NDA. A 500 mL glass column was packed with 40 g of American Norit peat carbon and 92 g of Norit Cwood carbon using a bed of glass wool to support the carbon. After flushing the column with 500 mL of 2.4 percent TMEA in water, the NDA-TMEA solution was passed through the column at room temperature at a rate of 8–15 mL/minute. After the initial 3050 g of material had been collected from the column (containing 449 g of 2,6-NDA) a second fraction was collected weighing 1707 g and containing 310 g of 2,6-NDA(dry basis)

A portion of this second fraction was dried to determine solids content and analyzed for color and by liquid chromatography. Results presented in Table 1 show that sample NDA-2 contained only 0.005 weight percent monocarboxylic acid compared to 0.15 percent in the feedstock indicating over 96 percent removal of the monocarboxylic acids. The color of sample NDA-2 was, also, significantly improved over the feedstock with an increase in the L* (100 is white) of 9 units and a decrease in the b* (0 is white) of 2 units.

After a total of 1245 g of crude 2,6-NDA had passed through the column, the column was washed with a mixture of 49 percent methanol, 49 percent water, and 2 percent trimethylamine. A portion of this wash was dried down to yield 3.1 g of a solid material and identified as ECReg which had composition shown in Table 1 under as ECReg. The high content of monocarboxylic acids in this sample, 13.6 percent, demonstrates that the carbon did preferentially retain these acids and concentrated them by about 100 times over the composition in the crude 2,6-NDA. This high separation factor for the monocarboxylic acids in the presence of a large excess of the 2,6-NDA is a unique feature of this invention. The ability to remove these monocarboxylic acids by reactivation is also a unique feature of this invention which is also illustrated by results presented in Table 2.

A 600 g portion of the second fraction (NDA-2) was neutralized by the addition of 390 g of 20 percent acetic acid. The resultant precipitate of 2,6-NDA was filtered and dried to yield 106.6 g of dry 2,6-NDA cake, identified as NDA-4. This drying step at 120° C. yielded 2,6-NDA containing only 55 ppm of nitrogen. Results presented in Table 1 show that sample NDA-4 contained 0.01 weight percent monocarboxylic acid compared to 0.15 percent in the feedstock indicating over 93 percent removal of the monocarboxylic acids. Also, 0.7 g of dried mother liquor was identified as NDA-5 for analysis. Selective precipitation improved the 2,6-NDA purity to over 99.5 percent as shown in Table 1. This step greatly reduced the concentration of several other impurities including the terephthalic acid, the naphthalene triacids, and the unknown impurities as demonstrated by the composition of the mother liquor in NDA-5.

Example 2

This example illustrates reactivation in accordance with the present invention of carbon adsorbent loaded with salts of mono functional aromatic impurities. Since the carbon bed removes relatively large amounts of impurities, it rapidly becomes exhausted and the capacity for removal of monocarboxylic acids is exhausted. An important feature of this invention is, therefore, a method of carbon reactivation that allows re-use of the same carbon for many cycles without replacement. The results are demonstrated by samples NDA-a to NDA-f in Table 2.

A 12 inch by 0.8 inch internal diameter 316 SS column was packed with 11.2 g of Norit Cwood carbon and used for purification of crude 2,6-NDA as in the Example 1. The composition of the crude feedstock for these examples is listed as NDA-a in Table 2. Fractions collected during purification runs were analyzed and the monocarboxylic acid content and color were monitored. When the column effluent analyses indicated that monocarboxylic acid content exceeded about 0.1 percent, the column was reactivated. The reactivation was conducted by passing 3 to 10 column volumes of an organic solvent mixture at 20° to 120° C. through the column to remove the adsorbed impurities. The organic solvent was then removed by washing with a water/TMeA mixture before the next adsorption cycle. Several solvents were used successfully including various ratios of tetrahydrofuran/water/trimethylamine, various ratios of tetrahydrofuran/ethanol/water/trimethylamine, and various ratios of ethanol/water/trimethylamine.

The column effluent analyses following the third regeneration (the fourth adsorption cycle) are listed in Table 2 as samples NDA-b to NDA-d. These examples show that the amount of monocarboxylic acid left in the 2,6-NDA after carbon treatment increases as the carbon becomes "saturated". After 8.6 g of 2,6-NDA had been treated per gram of carbon, the monocarboxylic acid content of the dried column effluent was 0.055 percent. The carbon was then reactivated and additional adsorption cycles were performed. Examples 6e and 6f are data collected after the seventh carbon reactivation. These examples indicate performance of the carbon similar to that obtained after the third reactivation with 0.07 percent of monocarboxylic acids in the treated 2,6-NDA after passage of 8.2 g of 2,6-NDA/g of carbon. These examples thus demonstrate that a single bed of carbon can be reused many times. The ability to reactivate the carbon at mild conditions with low-cost reagents makes this invention economically attractive.

TABLE 1

Purification of Crude Solids by Reacting with Trimethylene, Adsorption and Selective Precipitation to Recover Purified 2,6-Naphthalene Dicarboxylic Acid

| Sample ID | NDA-1 | NDA-2 | ECReg | NDA-4 | ML |
|---|---|---|---|---|---|
| | | Color | | | |
| L* | 86.7 | 95.7 | | 96.7 | |
| a* | 1.0 | −1.0 | | −1.3 | |
| b* | 9.6 | 7.4 | | 7.8 | |
| | | Weight Percent by LC analysis | | | |
| TA | 0.16 | 0.17 | 0.01 | 0.03 | 25.33 |
| NTA | 0.19 | 0.19 | 0.32 | 0.04 | 21.15 |
| NDA | 98.84 | 98.53 | 39.90 | 99.55 | 14.10 |
| BNDA | 0.0 | 0.0 | 0.01 | 0.0 | 2.10 |
| 6FNA | 0.094 | 0.004 | 5.793 | 0.003 | 0.026 |
| 2-NA | 0.059 | 0.001 | 7.84 | 0.01 | 0.00 |
| MNA | 0.00 | 0.00 | 0.95 | 0.00 | 0.00 |
| Other | 0.657 | 1.11 | 45.18 | 0.36 | 37.30 |

TABLE 1-continued

Purification of Crude Solids by Reacting with Trimethylene, Adsorption and Selective Precipitation to Recover Purified 2,6-Naphthalene Dicarboxylic Acid

| Sample ID | NDA-1 | NDA-2 | ECReg | NDA-4 | ML |
|---|---|---|---|---|---|

TA is terephthalic acid. NTA is naphthalene triacids. NDA is 2,6-naphthalene dicarboxylic acid (by difference). BNDA is 1-Bromo-2,6-naphthalene dicarboxylic acid. 6FNA is 6-formyl-2-naphthoic acid. 2-NA is 2-naphthoic acid. MNA is 2-methyl-6-naphthoic acid. Other is uncalibrated.

TABLE 2

Demonstration of Carbon Reactivation

| ID | NDA-a | NDA-b | NDA-c | NDA-d | NDA-e | NDA-f |
|---|---|---|---|---|---|---|
| | Weight Percent by LC analysis | | | | | |
| TLMA | 0.037 | 0.030 | 0.027 | 0.038 | 0.000 | 0.000 |
| TA | 0.091 | 0.091 | 0.091 | 0.094 | 0.100 | 0.083 |
| NDA | 96.859 | 98.013 | 98.140 | 98.030 | 98.402 | 98.203 |
| 6FNA | 0.357 | 0.014 | 0.042 | 0.071 | 0.019 | 0.071 |
| MNA | 0.034 | 0.000 | 0.013 | 0.012 | 0.000 | 0.000 |
| Other | 2.623 | 1.852 | 1.687 | 1.755 | 1.479 | 1.643 |
| Sum MCA | 0.391 | 0.014 | 0.055 | 0.083 | 0.019 | 0.071 |
| Treated | | 5.74 | 8.6 | 10.54 | 5.68 | 8.21 |

TMLA is trimetallic acid. TA is terephthalic acid. NDA is 2,6-naphthalene dicarboxylic acid (by difference). 6FNA is 6-formyl-2-naphthoic acid. MNA is 2-methyl-6-naphthoic acid. Other is uncalibrated. Sum MCA is total of monocarboxylic acids. Treated is 6 grams of 2,6-NDA had been treated per gram of carbon.

For the purposes of the present invention, "predominantly" is defined as more than about fifty per cent. "Substantially" is defined as occurring with sufficient frequency or being present in such proportions as to measurably affect macroscopic properties of an associated compound or system. Where the frequency or proportion for such impact is not clear substantially is to be regarded as about twenty per cent or more. The term "Essentially" is defined as absolutely except that small variations which have no more than a negligible effect on macroscopic qualities and final outcome are permitted, typically up to about one percent.

Examples have been presented and hypotheses advanced herein in order to better communicate certain facets of the invention. The scope of the invention is determined solely by the scope of the appended claims.

That which is claimed is:

1. An integrated process for preparation of a purified aromatic polycarboxylic acid obtained by liquid-phase oxidation of a corresponding aromatic compound having at least two oxidizable alkyl or acyl ring substituents or an oxidizable alkyl and acyl ring substituent in non-adjacent positions, with a dioxygen-containing gas in a solvent at an elevated temperature and pressure and in the presence of an oxidation catalyst comprising a heavy metal component to prepare crude solids containing the desired aromatic polycarboxylic acid wherein the level of monofunctional, difunctional and/or trifunctional aromatic impurities retained by the crude solids is equal to or less than about 5 percent, based upon the weight of polycarboxylic acid present, which process comprises:

(a-1) introducing crude solids containing the desired aromatic polycarboxylic acid into an aqueous solution of a polyalkyl amine containing up to about 20 carbon atoms while maintaining the solution at a level of pH in a range upward from about 7 and at temperature and pressure sufficient to maintain the solution substantially in the liquid phase, to form soluble salts of the polycarboxylic acid and one or more of the monofunctional, difunctional and/or trifunctional aromatic impurities in the aqueous solution;

(b-1) contacting the aqueous solution with an immiscible liquid solvent or solid adsorbent, transferring a substantial fraction of the salt of at least one of the monofunctional aromatic impurities from the aqueous solution to the immiscible liquid solvent or solid adsorbent, and recovering therefrom purified aqueous solution;

(c-1) acidifying the purified aqueous solution of the polyalkyl amine salt of the polycarboxylic acid with a carboxylic acid containing from 1 to 6 carbon atoms to a level of pH in a range downward from about 6.7 to form a slurry of precipitated polycarboxylic acid in mother liquor which retains a substantial fraction of the soluble salts of the trifunctional aromatic impurities, and (d-1) recovering from the slurry purified polycarboxylic acid product which contains less than about 1 percent of the mono-functional and/or trifunctional aromatic impurities, based upon the weight of the polycarboxylic acid present.

2. The integrated process for preparation of a purified aromatic polycarboxylic acid according to claim 1 wherein at least a portion of the polyalkyl amine in the aqueous solution used in (a-1) is derived from the mother liquor subsequent to recovery therefrom of the purified polycarboxylic acid product.

3. The integrated process for preparation of a purified aromatic polycarboxylic acid according to claim 1 wherein the contacting in (b) of the aqueous solution is carried out by passing the solution through at least a first particulate bed comprising active carbon and/or other solid adsorbent, until the active carbon in the first bed is loaded with the salt of at least one of the monofunctional aromatic impurities, and thereafter treating the loaded bed to regenerate the active carbon and/or other solid adsorbent for further use by a reconditioning process which comprises; (i) displacing the aqueous solution containing the polycarboxylic acid from the bed, (ii) passing an aqueous solution of a polar organic solvent containing from about 1 to about 10 carbon atoms, through the bed to desorb the salts of the impurities, and (iii) flushing the polar organic solvent from the bed with water.

4. The integrated process for preparation of a purified aromatic polycarboxylic acid according to claim 1 wherein the desired aromatic polycarboxylic acid being purified is selected from the group consisting of terephthalic acid formed by the oxidation of para-xylene, isophthalic acid formed by the oxidation of metaxylene, 1,5-naphthalene dicarboxylic acid formed by the oxidation of a 1,5-dialkylnaphthalene, 2,7-naphthalene dicarboxylic acid formed by the oxidation of a 2,7-dialkylnaphthalene, and 2,6-naphthalene dicarboxylic acid formed by the oxidation of a 2,6-dialkylnaphthalene.

5. The integrated process for preparation of a purified aromatic polycarboxylic acid according to claim 1 wherein the carboxylic acid is selected from a group consisting of formic acid, acetic acid, propionic acid, n-butyric acid, isobutyric acid, n-valeric acid, trimethylacetic acid and caproic acid, and mixtures thereof.

6. The integrated process for preparation of a purified aromatic polycarboxylic acid according to claim 1 wherein (a-1) is carried out at temperatures in a range from about 60° F. to about 215° F. and at a pressure sufficient to maintain at least about 80 percent of the polyalkyl amine in the aqueous solution.

7. The integrated process for preparation of a purified aromatic polycarboxylic acid according to claim 1 wherein the polyalkyl amine is selected from the group consisting of trimethylamine and triethylamine.

8. The integrated process for preparation of a purified aromatic polycarboxylic acid according to claim 7 wherein the mother liquor is fractionated as by distillation into at least a first distillate fraction rich in polyalkyl amine and essentially free of carboxylic acid, and another fraction rich in the carboxylic acid and essentially free of polyalkyl amine.

9. The integrated process for preparation of a purified aromatic polycarboxylic acid according to claim 8 wherein at least a portion of the distillate fraction rich in polyalkyl amine is recycled into the aqueous solution used in (a-1).

10. The integrated process for preparation of a purified aromatic polycarboxylic acid according to claim 8 wherein at least a portion of the fraction rich in carboxylic acid is recycled into the monocarboxylic acid used in (c-1).

11. An integrated process for preparation of a purified 2,6-naphthalene dicarboxylic acid obtained by liquid-phase oxidation of a 2,6-dialkylnaphthalene with a dioxygen-containing gas in a solvent at an elevated temperature and pressure and in the presence of an oxidation catalyst comprising a heavy metal component to prepare crude solids containing the desired purified 2,6-naphthalene dicarboxylic acid wherein the level of monofunctional, difunctional and/or trifunctional aromatic impurities retained by the crude solids is equal to or less than about 3 percent, based upon the weight of the crude 2,6-naphthalene dicarboxylic acid present, which process comprises:

(a-11) introducing crude solids containing 2,6-naphthalene dicarboxylic acid into aqueous solution of a trialkyl amine containing up to about 20 carbon atoms at temperatures in a range from about 68° F. to about 215° F. and sufficient pressure to maintain at least about 80 percent of the trialkyl amine in the aqueous, while maintaining the solution at a level of pH in a range upward from about 7 to form soluble salts of the 2,6-naphthalene dicarboxylic acid and one or more of the monofunctional and/or trifunctional aromatic impurities in the aqueous solution;

(b-11) passing the aqueous solution through at least a first particulate bed of adsorbent comprising active carbon, transferring a substantial fraction of the salt of at least one of the monofunctional aromatic impurities from the aqueous solution to the immiscible liquid solvent or solid adsorbent, and recovering therefrom purified aqueous solution; until the active carbon in the first bed is loaded with the salt of at least one of the monofunctional aromatic impurities; thereafter (c-11) treating the loaded bed to regenerate the active carbon and/or other solid adsorbent for further use by a reconditioning process which comprises; (i) displacing the aqueous solution containing the polycarboxylic acid from the bed, (ii) passing an aqueous solution of a polar organic solvent containing from about 1 to about 10 carbon atoms, through the bed to desorb the salts of the impurities, and (iii) flushing the polar organic solvent from the bed with water; and (d-11) repeating step (b-11).

12. The integrated process for preparation of a purified 2,6-naphthalene dicarboxylic acid according to claim 11 further comprising;

(e-12) acidifying the purified aqueous solution of the amine salt of the 2,6-naphthalene dicarboxylic acid with a carboxylic acid containing from 1 to 6 carbon atoms to a level of pH in a range downward from about 6.9 to form a slurry of precipitated 2,6-naphthalene dicarboxylic acid in mother liquor which retains a substantial fraction of the soluble salts of the trifunctional aromatic impurities, and (f-12) recovering from the slurry purified 2,6-naphthalene dicarboxylic acid product which contains less than about 1 percent of the monofunctional and/or trifunctional aromatic impurities, based upon the weight of the 2,6-naphthalene dicarboxylic acid present.

13. The integrated process for preparation of a purified 2,6-naphthalene dicarboxylic acid according to claim 12 wherein at least a portion of the trialkyl amine in the aqueous solution used in (a) is derived from the mother liquor subsequent to recovery therefrom of the purified polycarboxylic acid product.

14. The integrated process for preparation of a purified 2,6-naphthalene dicarboxylic acid according to claim 11 wherein the crude solid contains one or more monofunctional aromatic compound selected from the group consisting of 2-naphthoic acid, 2-methyl-6-naphthoic acid and 2-formyl-6-naphthoic acid.

15. The integrated process for preparation of a purified 2,6-naphthalene dicarboxylic acid according to claim 12 wherein (e-12) is carried out to a level of pH in a range from about 6.7 to about 5.0 using a carboxylic acid selected from a group consisting of formic acid, acetic acid, propionic acid, n-butyric acid, and mixtures thereof.

16. The integrated process for preparation of a purified 2,6-naphthalene dicarboxylic acid according to claim 12 wherein (a-11) is carried out at temperatures in a range from about 68° F. to about 175° F. and sufficient pressure to maintain at least about 80 percent of the trialkyl amine in the aqueous solution.

17. The integrated process for preparation of a purified 2,6-naphthalene dicarboxylic acid according to claim 12 wherein the trialkyl amine is selected from the group consisting of trimethylamine and triethylamine, wherein pH of the aqueous solution is reduced in (c) to a level of pH in a range from about 6.7 to about 5.0 by admixing with acetic acid, and wherein the purified 2,6-naphthalene dicarboxylic acid has color measurements of L*-values in a range upward from about 91 to about 99, and of b*-values in a range downward from about 10 to about of 3.

18. The integrated process for preparation of a purified 2,6-naphthalene dicarboxylic acid according to claim 17 further comprising;

(g-18) fractionating at least portion of the mother liquor by distillation subsequent to recovery therefrom of the purified polycarboxylic acid product to recover at least a first aqueous fraction rich in the trialkyl amine which first fraction contains less than 5 percent of the carboxylic acid, and another aqueous fraction rich in the carboxylic which fraction contains less than 10 percent of the trialkyl amine.

19. The integrated process for preparation of a purified 2,6-naphthalene dicarboxylic acid according to claim 18 wherein the fraction rich in the trialkyl amine is, predominantly, recycled into the aqueous solution used in (a-11), and wherein the fraction rich in the carboxylic acid is, predominantly, recycled with the carboxylic acid used in (e-12).

20. An integrated process for preparation of a purified 2,6-naphthalene dicarboxylic acid obtained by liquid-phase oxidation of a 2,6-dialkylnaphthalene with a dioxygen-containing gas in a solvent at an elevated temperature and pressure and in the presence of an oxidation catalyst comprising a heavy metal component to prepare crude solids containing the desired purified 2,6-naphthalene dicarboxylic acid wherein the level of monofunctional, difunctional and/or trifunctional aromatic impurities retained by the crude solids is equal to or less than about 3 percent, based upon the weight of the crude 2,6-naphthalene dicarboxylic acid present, which process comprises:

(a-20) introducing crude solids containing 2,6-naphthalene dicarboxylic acid into aqueous solution of a trialkyl amine containing up to about 20 carbon atoms at temperatures in a range from about 68° F. to about 215° F. and sufficient pressure to maintain at least about 80 percent of the trialkyl amine in the aqueous, while maintaining the solution at a level of pH in a range upward from about 7 to form soluble salts of the 2,6-naphthalene dicarboxylic acid and one or more of the monofunctional and/or trifunctional aromatic impurities in the aqueous solution;

(b-20) contacting the aqueous solution with an immiscible liquid solvent or solid adsorbent, transferring a substantial fraction of the salt of at least one of the monofunctional aromatic impurities from the aqueous solution to the immiscible liquid solvent or solid adsorbent, and recovering therefrom purified aqueous solution;

(c-20) heating the purified aqueous solution of the amine salt of the 2,6-naphthalene dicarboxylic acid to elevated temperatures in a range upward from about 70° C. to form a slurry of precipitated 2,6-naphthalene dicarboxylic acid in mother liquor which retains a substantial fraction of the soluble salts of the trifunctional aromatic impurities, and (d-20) recovering from the slurry purified 2,6-naphthalene dicarboxylic acid product which contains less than about 1 percent of the monofunctional and/or trifunctional aromatic impurities, based upon the weight of the 2,6-naphthalene dicarboxylic acid present.

* * * * *